United States Patent [19]

Gasser et al.

[11] 4,332,743

[45] Jun. 1, 1982

[54] PROCESS FOR THE LIQUID PHASE PRODUCTION OF $C_1$ TO $C_3$ CARBOXYLIC ACIDS

[75] Inventors: Clive G. Gasser, Cottingham; John Russell, Hull, both of England

[73] Assignee: BP Chemicals Limited, London, England

[21] Appl. No.: 6,092

[22] Filed: Jan. 24, 1979

[30] Foreign Application Priority Data

Jan. 27, 1978 [GB] United Kingdom ............... 03320/78

[51] Int. Cl.$^3$ ..................... C07C 27/10; C07B 3/00
[52] U.S. Cl. ................................ 562/512.2; 562/549
[58] Field of Search ..................... 562/549; 260/451

[56] References Cited

U.S. PATENT DOCUMENTS

| | | | |
|---|---|---|---|
| 2,265,948 | 12/1941 | Loder | 562/549 |
| 2,934,551 | 4/1960 | Stringer | 260/451 |
| 2,969,380 | 1/1961 | Selwitz | 562/549 |
| 3,103,535 | 9/1963 | Whitfield et al. | 562/531 |

FOREIGN PATENT DOCUMENTS

| | | | |
|---|---|---|---|
| 550933 | 5/1932 | Fed. Rep. of Germany | . |
| 743991 | 1/1956 | United Kingdom | 562/542 |
| 1403196 | 8/1975 | United Kingdom | 562/549 |

*Primary Examiner*—Werren B. Lone
*Attorney, Agent, or Firm*—Brooks, Haidt, Haffner & Delahunty

[57] ABSTRACT

$C_1$ to $C_3$ mono-carboxylic acids, including a substantial proportion of acetic acid, are produced by oxidizing a paraffinic hydrocarbon feedstock with molecular oxygen at a temperature in the range 150° to 250° C. and at an elevated pressure sufficient to maintain the reactants in the liquid phase in the presence as catalyst, of phosphoric acid and/or a phosphate of one or more metals of Groups I and II of the Periodic Table, in particular sodium or potassium. In an alternative embodiment of the invention a co-catalyst in the form of one or more metals of variable valency, particularly manganese, is incorporated in the reactants. The reaction products are recovered by distillation.

8 Claims, No Drawings

PROCESS FOR THE LIQUID PHASE PRODUCTION OF $C_1$ TO $C_3$ CARBOXYLIC ACIDS

The present invention relates generally to the production of $C_1$ to $C_3$ carboxylic acids by the liquid phase oxidation of a paraffinic hydrocarbon feedstock and in particular to the addition of phosphoric acid and/or a phosphate of one or more metals of Groups I and II of the Periodic Table to such oxidations for the purpose of increasing the selectivity of acetic acid.

The liquid phase oxidation of a paraffinic hydrocarbon feedstock with molecular oxygen at elevated temperature and pressures to produce $C_1$ to $C_3$ carboxylic acids is a well known process and is described, for example, in British Patent Specification Nos. 743,989; 743,990; 743,991; 767,290 and 771,992. The products produced by this process may be classified as (a) volatile non-acidic oxidation products of boiling-point up to 99° C. in the presence of water, generally referred to as "low boilers" or "light ends", (b) water, (c) aliphatic mono-carboxylic acids of 1 to 3 carbon atoms and (d) higher boiling materials, including acids, otherwise known as "heavy ends".

The use of compounds of metals of variable valency as catalysts in paraffin oxidation processes for the purpose of increasing the overall selectivity to acids is described in the very early patent specifications referred to hereinbefore. In recent years it has been recognised that improving not only the overall selectivity to acids but also the relative amounts of particular acids in the oxidation product is a desirable objective. Thus it has been reported comparatively recently that the use of a cobalt catalyst containing at least one other metal selected from sodium, potassium, copper, magnesium, calcium, zinc, cadmium, barium, aluminium, tin, lead, nickel, or iron as catalyst increases the ratio of the yield of acetic acid to the yield of formic acid. Also British Patent Specification No 1,403,196 describes the use of a manganese compound in a concentration of from 1 to 50 parts per million based on the total weight of reaction mixture as catalyst in order to achieve improved selectivies to acetic acid on oxygen consumed. Furthermore British Patent Specification No 1,396,747 describes the addition of molybdenum in the +6 oxidation state to paraffin oxidations, again for the purpose of increasing the selectivity to acetic acid.

It has now been found that the selectivity to acetic acid can be increased by the addition to the oxidation reaction of phosphoric acid and/or a phosphate of one or more metals of Groups I and II of the Periodic Table.

Accordingly the present invention provides a process for the production of $C_1$ to $C_3$ mono-carboxylic acids, including a substantial proportion of acetic acid, by oxidising in a reaction zone a paraffinic hydrocarbon feedstock with molecular oxygen at a temperature in the range from 150° to 250° C. and at an elevated pressure sufficient to maintain the reactants in the liquid phase characterised in that there is added to the reactants a compound comprising phosphoric acid and/or a phosphate of one or more metals of Groups I and II of the Periodic Table.

Any of the known types of apparatus in which molecular oxygen is intimately contacted with liquid feed may form the reaction zone. An example of a suitable form of apparatus is a vertical stainless steel tower containing a coaxial draught tube open at both ends thereof. In operation the tower is filled to at least the height of the top of the draught tube with liquid reactant, molecular-oxygen containing gas is introduced into the tower near the base and external to the draught tube. The mixture of gas and liquid rises until it is level with the top of the draught tube, whereupon the gas disengages from the liquid and the liquid descends through the draught tube to the base of the reactor where the cycle is repeated.

The paraffinic hydrocarbon is preferably a paraffin containing from 4 to 8, even more preferably 5 to 7, carbon atoms in the molecule or a mixture thereof. The paraffin may be a straight-chain paraffin, used either alone or in admixture with branched-chain and cyclic paraffins. Any branched-chain paraffins present in the hydrocarbon feed preferably have one or more methyl-branch chains. Paraffinic fractions may be used; preferably any such fraction boils at a temperature not exceeding 100° C. It is particularly preferred to use a fraction having a boiling range of about 15° to about 95° C.

Examples of suitable feedstocks which may be used are straight-run petroleum fractions; the products from the aluminium chloride-catalysed isomerisation of predominantly straight-chain paraffins having 4 to 8 carbon atoms or from other isomerisation processes known in the art; the products obtained by the alkylation of $C_2$ to $C_4$ olefins with isoparaffins; or alternatively the product obtained by hydrogenation of the mono-olefins produced by dimerisation of lower olefins such as propylene and isobutene. An example of a commercially available paraffinic hydrocarbon feedstock suitable for the process of the invention is a straight run gasoline fraction from petroleum boiling between about 15° and 95° C.

The molecular oxygen may be fed to the process in the form, for example, of air or mixtures of gas richer or poorer in molecular oxygen than air.

The elevated temperature is preferably in the range from 160° to 200° C. The pressure is chosen such that the reactants are maintained in the liquid phase. Generally pressures in the range 30 to 70 bar will be found suitable.

It is preferred to operate the process in such a manner that substantially all the oxygen fed is absorbed. Thus the concentration of oxygen in the gas leaving the oxidation zone is preferably maintained at not more than 1% wt/wt. The desired rate of absorption may be obtained by adjusting the reaction temperature.

Phosphoric acid may suitably be added in the form of orthophosphoric acid. It may however be added in the form of meta- or pyrophosphoric acid. Group I and Group II metal phosphates may be added in the form of ortho-, meta- or pyrophosphates. The specific phosphorus containing compound is not believed to be critical but it should preferably be soluble in the reaction medium at the concentrations used in order to avoid operational problems. Suitable phosphates include sodium and potassium phosphates. The phosphoric acid and/or phosphate salt may suitably be added in an amount in the range from 0.1 to 1000 ppm, preferably from 0.5 to 100 ppm, calculated as elemental phosphorus.

As hereinbefore mentioned, metals of variable valency, in the form of soluble salts thereof, are known paraffin oxidation catalysts. It has now been found that the increase in selectivity to acetic acid attending the addition of phosphoric acid and/or a phosphate of one or more metals of Groups I and II of the Periodic Table can be further enhanced by the addition of a salt of certain metals of variable valency.

Thus in a further embodiment of the present invention in addition to adding a compound comprising phosphoric acid and/or a phosphate of one or more metals of Groups I and II of the Periodic Table there is also added a compound of a metal of variable valency. Metals of variable valency which may be used include iron, chromium, manganese, cobalt, nickel and molybdenum, of which manganese is preferred. The metal is preferably added in the form of a soluble salt thereof. Examples of suitable soluble salts are the salts of carboxylic acids such as naphthenates, octanoates or acetates. Alternatively inorganic compounds such as the metal salts of carbonic or nitric acid may be employed. Preferably the compound of a metal of variable valency is manganese acetate. When phosphoric acid or a phosphate of one or more metals of Groups I and II is added in addition to a compound of a metal of variable valency the total amount of added compounds may suitably be in the range from 0.1 to 1000, preferably from 0.5 to 100 ppm, calculated as elemental phosphorus plus metal of variable valency.

The process may be operated batchwise or continuously. It is preferred to operate the process continuously and feed the added compound continuously in order to maintain its concentration in the reaction zone within the desired range. The rate at which the added compound is fed during continuous operation will depend on the rate at which the compound is lost from the reaction zone, which in turn will depend upon whether the reaction product is recovered from the reaction zone as a vapour or as a liquid or as a vapour/liquid mixture. The added compound may suitably be fed to the reaction zone in admixture with the paraffinic hydrocarbon feedstock or a $C_1$ to $C_3$ aliphatic mono-carboxylic acid or water. The content of the added compound in the reaction zone may be maintained at the desired level by measuring the volume of liquid product withdrawn from the reaction zone and adjusting the amount of the compound fed to the zone to make up for that lost from the zone in the liquid product on the assumption that the content of the compound in the liquid product withdrawn is the same as that in the reaction zone and that none of the compound is deposited therein.

The reaction product may be recovered from the reaction zone and worked up to give individual $C_1$ to $C_3$ carboxylic acids in any convenient manner. Thus the reaction product may be recovered from the process as a liquid stream, which may be distilled to remove the low-boiling compound or "light ends" overhead. The residue from this distillation may be subjected to further distillation to recover water and lower carboxylic acids overhead, leaving higher boiling materials as residue. The mixture of water and lower carboxylic acids may then be subjected to further distillation to remove water and to recover formic, acetic and propionic acids and, if desired, butyric acid. Suitable methods of distillation are well-known in the art. The light ends may be recycled directly to the reaction zone. Alternatively, acetone may be recovered from the "light ends" before recycle to the reaction zone.

The invention will now be described with reference to the following Examples and Comparison Tests.

COMPARISON TEST 1

The reaction zone employed was a 5 ft×4 inch diameter stainless steel cylindrical reactor fitted with an internal draught tube to promote liquid circulation and heated by means of an oil jacket. The paraffinic hydrocarbon feed was a straight-run naphtha with a boiling range of ca 40° to 110° C., containing 27% naphthenes and 6% aromatics, the remainder being paraffins. All feed and recycle streams were fed at the base of the reactor. Air was introduced at the base of the reactor through a sparge ring external to the draught tube. The pressure within the reactor was maintained at 48.3 bar and the temperature at 170° to 174° C. to give an oxygen absorption rate of 0.26 kg/l/h.

Liquid products were withdrawn from the base of the reactor through a pressure reducing valve. Organic vapours issuing from the head of the reactor were condensed and returned. Waste gases were vented to atmosphere. The liquid product removed from the base of the reactor was fed to a fractional distillation column. This was a packed glass column operating at atmospheric pressure. The base of the column was maintained at a temperature of 105° C. Low-boiling compounds (ie, materials boiling at temperatures up to 99° C. in the presence of water, otherwise known as "light ends") were removed overhead, some being returned to the column as reflux, the rest being returned to the reactor after recovering acetone therefrom. The product from the base of the column was analysed by gas-liquid chromatography to determine the yields of $C_1$–$C_3$ acids.

The selectivities on oxygen consumed averaged over four such tests are given in the following Table 1.

This is not an Example according to the invention and is included for the purpose of comparison only.

EXAMPLE 1

The procedure described in Comparison Test 1 was repeated, except that an aqueous phosphoric acid solution was fed to the reactor at such a rate as to maintain the phosphorus concentration in the liquid product withdrawn from the base of the reactor at 20 ppm. Furthermore, the reaction temperature was allowed to rise to 179° C. to keep the oxygen absorption rate constant.

The selectivities on oxygen consumed are given in the following Table 1.

EXAMPLE 2

The procedure described in Comparison Test 1 was repeated, except that phosphoric acid and manganese acetate in aqueous solution were fed to the reactor at such a rate as to maintain the phosphorus and manganese concentrations in the liquid product withdrawn from the base of the reactor at 10 ppm and 10 ppm respectively. Furthermore, the reaction temperature rose to 184° C.

The selectivities on oxygen consumed are given in the following Table 1.

EXAMPLE 3

Example 2 was repeated, except that manganese acetate was replaced by nickel acetate.

The selectivities on oxygen consumed are given in the following Table 1.

EXAMPLE 4

Example 2 was repeated, except that manganese acetate was replaced by cobalt acetate. The reaction temperature fell to 172° C.

The selectivities on oxygen consumed are given in the following Table 1.

All the Examples 1 to 4 demonstrate an improvement in acetic acid selectively based on oxygen absorbed, the improvement being most marked in Example 2 in which phosphoric acid and manganese acetate were added in combination. Whilst the selectivity to formic acid in Examples 1 to 3 remained substantially unaltered, the selectivity to propionic acid was improved also. The selectivity to formic acid was approximately halved by the addition of cobalt acetate in Example 4 and, whilst the selectivity to acetic acid and propionic acid was increased, this was not so marked as in the case of the addition of phosphoric acid alone (Example 1).

TABLE 1

Oxidation Conditions: Reaction pressure 48.3 bar
Oxygen absorption rate 0.26 kg/l.h
PLE/$O_2$ ratio* 0.7:1

| | | Example | | | |
|---|---|---|---|---|---|
| | Comparison Test 1 | 1 | 2 | 3 | 4 |
| ADDITIVE* | None (4 baseline experiments) | 20 ppm P | 10 ppm P + 10 ppm Mn | 10 ppm P + 10 ppm Ni | 10 ppm P + 10 ppm Co |
| Reaction Temperature °C. | 170–174 | 179 | 184 | 184 | 172 |
| Selectivities on $O_2$ Absorbed % w/w | | | | | |
| Formic Acid | 10.5–11.2 | 11.3 | 11.6 | 11.2 | 5.5 |
| Acetic Acid | 32–34 | 37.7 | 40.5 | 38.5 | 36.3 |
| Propionic Acid | 6.2–7.0 | 8.2 | 7.8 | 8.4 | 8.0 |
| Acetone | 7.1–8.5 | 8.5 | 9.0 | 8.6 | 8.0 |

*PLE/$O_2$ ratio is the weight ratio of "light ends" leaving the reactor to oxygen reacted.

COMPARISON TEST 2

The procedure of Comparison Test 1 was followed except that a better quality naphtha feedstock containing 84% paraffins, 13% naphthenes and 3% aromatics was used. The rate of oxygen absorption, the PLE/$O_2$ ratio and the operating pressure were the same as used in Comparison Test 1 but the temperature was increased to 181° C.

The selectivities on oxygen absorbed are given in the following Table 2.

This is not an example illustrating the present invention because no phosphoric acid or phosphate was added.

EXAMPLE 5

The procedure of Comparison Test 2 was repeated except that an aqueous solution of ortho-phosphoric acid was fed to the reactor at such a rate as to maintain the phosphorus concentration in the liquid product withdrawn from the base of the reactor at 2 ppm. Furthermore the reaction temperature was increased to 188° C. to maintain the oxygen absorption rate constant.

The selectivities on oxygen absorbed are given in the following Table 2.

EXAMPLE 6

Example 5 was repeated except that the phosphorus concentration was increased to 10 ppm and the temperature to 194° C.

The selectivities on oxygen absorbed are given in the following Table 2.

EXAMPLE 7

Example 5 was repeated except that the phosphorus concentration was increased to 20 ppm and the temperature was increased to 193° C.

The selectivities on oxygen absorbed are given in the following Table 2.

TABLE 2

| | Comparison Test | | | |
|---|---|---|---|---|
| Example | 2 | 5 | 6 | 7 |
| Concentration of phosphoric acid in reactor product (ppm as P) | 0 | 2 | 10 | 20 |
| Reaction temperature (°C.) | 181 | 188 | 194 | 193 |
| Selectivities on $O_2$ Absorbed, (% w/w) | | | | |
| Formic Acid | 12.2 | 13.0 | 12.0 | 12.0 |
| Acetic Acid | 42.0 | 45.7 | 47.6 | 48.9 |
| Propionic Acid | 7.6 | 7.9 | 8.2 | 8.7 |
| Acetone | 8.9 | 8.4 | 9.3 | 8.8 |

In all of the Examples 5 to 7 the selectivities to both acetic and propionic acids increased with increasing phosphorus concentration.

COMPARISON TEST 3

The procedure of Comparison Test 2 was followed except that rather more acetone was extracted from the 'light ends' stream before this stream was returned to the oxidation reactor.

The selectivities on oxygen absorbed are given in the following Table 3.

This is not an example of the working of the present invention because no phosphoric acid or phoshate was added.

EXAMPLE 8

Comparison Test 3 was repeated except that an aqueous solution of ortho-phosphoric acid was fed to the reactor at such a rate as to maintain the phosphorus concentration in the liquid product withdrawn from the base of the reactor at 20 ppm, and the temperature was increased to 193° C. to maintain the oxygen absorption rate constant.

The selectivities on oxygen absorbed are given in the following Table 3.

EXAMPLE 9

Example 8 was repeated except that $Na_3PO_4$, trisodium ortho-phosphate, was added in place of ortho-phosphoric acid.

The selectivities on oxygen absorbed are given in the following Table 3.

EXAMPLE 10

Example 8 was repeated except that in place of ortho-phosphoric acid there was added $(NaPO_3)_6$, sodium hexametaphosphate, and the temperature was increased to 194° C.

The selectivities on oxygen absorbed are given in Table 3.

EXAMPLE 11

Example 8 was repeated except that in place of ortho-phosphoric acid there was added $Na_4P_2O_7$, sodium pyrophosphate, and the temperature was increased to 195° C.

TABLE 3

| Example | Comparison Test 3 | 8 | 9 | 10 | 11 |
|---|---|---|---|---|---|
| Additive used | None | $H_3PO_4$ | $Na_3PO_4$ | $(NaPO_3)_6$ | $Na_4P_2O_7$ |
| Concentration of additive in reactor product (ppm as P) | — | 20 | 20 | 20 | 20 |
| Reaction temperature (°C.) | 181 | 193 | 193 | 194 | 195 |
| Selectivities on $O_2$ Absorbed (% w/w) | | | | | |
| Formic Acid | 11.8 | 11.8 | 10.4 | 11.1 | 10.5 |
| Acetic Acid | 43.3 | 48.5 | 50.3 | 49.9 | 50.8 |
| Propionic Acid | 7.5 | 8.2 | 8.7 | 8.3 | 8.5 |
| Acetone | 11.0 | 11.1 | 11.2 | 11.9 | 11.4 |

In Examples 8 to 11 similar improvements in selectivity to acetic and propionic acids were observed for the different phosphates added.

EXAMPLE 12

Example 7 was repeated except that the oxygen absorption rate was adjusted to 87% of the value prevailing in the Example and the temperature was increased to 194° C.

The selectivities on oxygen absorbed are given in the following Table 4.

EXAMPLE 13

Example 12 was repeated except that, in addition to the ortho-phosphoric acid, manganese acetate was added at such a rate as to maintain the manganese concentration in the liquid product withdrawn from the base of the reactor at 10 ppm and the temperature was reduced to 193° C.

The selectivities on oxygen absorbed are given in the following Table 4.

EXAMPLE 14

Example 13 was repeated except that the ortho-phosphoric acid was added at such a rate as to maintain the phosphorus concentration in the liquid product withdrawn from the base of the reactor at 10 ppm, the manganese acetate feed rate remaining unchanged. The temperature was increased to 194° C.

The selectivities on oxygen absorbed are given in the following Table 4.

Examples 13 and 14 demonstrate the further improvement in selectivity to acetic acid consequent upon the addition of manganese, although the effect is less marked than with the poorer quality naphtha feedstock used in Example 2.

TABLE 4

| Example | 12 | 13 | 14 |
|---|---|---|---|
| Additives used | | | |
| Phosphoric Acid (ppm as P) | 20 | 20 | 10 |
| Manganese Acetate (ppm as Mn) | — | 10 | 10 |
| Reaction Temperature (°C.) | 194 | 193 | 194 |
| Selectivities on $O_2$ Absorbed (% w/w) | | | |
| Formic Acid | 12.4 | 12.1 | 12.3 |
| Acetic Acid | 48.8 | 49.6 | 49.8 |
| Propionic Acid | 8.8 | 8.6 | 8.3 |
| Acetone | 10.2 | 10.2 | 10.1 |

We claim:

1. In a process for the production of $C_1$ to $C_3$ monocarboxylic acids, including a substantial proportion of acetic acid, by oxidizing in a reaction zone a paraffinic hydrocarbon feedstock containing from 4 to 8 carbon atoms in the molecule with molecular oxygen at a temperature in the range from 150° to 250° C. and at an elevated pressure of 30 to 70 bar sufficient to maintain the reactants in the liquid phase, the improvement which comprises carrying out said oxidation in the presence of at least one added phosphorus-containing compound selected from the group consisting of phosphoric acids and phosphates of metals of Groups I and II of the Periodic Table in an amount in the range of from 0.5 to 100 ppm, calculated as elemental phosphorus.

2. A process according to claim 1 wherein said paraffinic hydrocarbon feedstock is a paraffinic fraction having a boiling range from about 15° to about 95° C.

3. A process according to claim 1 wherein said phosphate of a metal of Groups I and II of the Periodic Table is selected from phosphates of sodium and potassium.

4. A process according to claim 1 wherein, in addition to said phosphorus-containing compound, there is also added a compound of a metal of variable valency selected from iron, chromium, manganese, cobalt, nickel and molybdenum.

5. A process according to claim 4 wherein said metal of variable valency is manganese.

6. A process according to claim 1 wherein said process is operated in a continuous manner.

7. A process according to claim 1 wherein said reaction zone is fabricated in stainless steel.

8. In a process for the production of $C_1$ to $C_3$ monocarboxylic acids, including a substantial proportion of acetic acid, by oxidizing in a reaction zone a paraffinic hydrocarbon feedstock containing from 4 to 8 carbon atoms in the molecule with molecular oxygen at a temperature in the range from 150° to 250° C. and at an elevated pressure of 30 to 70 bar sufficient to maintain the reactants in the liquid phase, the improvement which comprises carrying out said oxidation in the presence of at least one added phosphorus-containing compound selected from the group consisting of phosphoric acids and phosphates of metals of Groups I and II of the Periodic Table in an amount in the range of from 0.1 to 1000 ppm, calculated as elemental phosphorus and in the absence of a compound of a metal of variable valency selected from the group consisting of iron, chromium, manganese, cobalt, nickel and molybdenum.

* * * * *